United States Patent [19]

Altshuler

[11] 4,366,822
[45] Jan. 4, 1983

[54] METHOD AND APPARATUS FOR BONE MARROW CELL SEPARATION AND ANALYSIS

[75] Inventor: John H. Altshuler, Englewood, Colo.

[73] Assignee: Applied Medical Devices, Inc., Englewood, Colo.

[21] Appl. No.: 99,579

[22] Filed: Dec. 3, 1979

[51] Int. Cl.$^3$ ............................................. A61B 10/00
[52] U.S. Cl. ................................... 128/753; 128/765
[58] Field of Search ............................. 128/749-753, 128/760, 276, 763, 765, 224, 234, 247, 218 R, 758; 210/952

[56] References Cited

U.S. PATENT DOCUMENTS

| | | | |
|---|---|---|---|
| 1,668,315 | 5/1928 | Hein | 128/247 |
| 3,000,805 | 9/1961 | Carritt et al. | 204/195 R |
| 3,224,434 | 12/1965 | Molomut et al. | 128/749 |
| 3,270,767 | 9/1966 | Hirsch | 128/247 X |
| 3,382,865 | 5/1968 | Worrall, Jr. | 128/762 |
| 3,470,867 | 10/1969 | Goldsmith | 128/753 |
| 3,706,305 | 12/1972 | Berger et al. | 128/762 |
| 3,736,932 | 5/1973 | Satchell | 128/218 R |
| 3,833,000 | 9/1974 | Bridgman | 128/762 |
| 3,889,657 | 6/1975 | Baumgarten | 128/758 |
| 3,889,682 | 6/1975 | Denis et al. | 128/762 |
| 3,965,889 | 6/1976 | Sachs | 128/764 |
| 3,976,529 | 8/1976 | Weichselbaum | 210/452 X |
| 3,977,403 | 8/1976 | Patel | 128/247 X |
| 4,008,718 | 2/1977 | Pitesky | 128/234 X |
| 4,083,706 | 4/1978 | Wiley | 128/276 X |
| 4,137,917 | 2/1979 | Cohen | 128/218 R |

OTHER PUBLICATIONS

Rywlin et al., "Bone Marrow Histologn, Aspiration vs. Biopsn", A.J.C.P., vol. 66, Sep., 1976, pp. 617–618.
Neiman et al., "The Relative Merits of Bone Marrow Biopsn and Particle Section Techniques", A.J.C.P., vol. 67:3, pp. 308–309.
O'Neil, "Bone Marrow Examinations", The Medical Journal of Australia, Jan., 1979, pp. 21–22.

Primary Examiner—Kyle L. Howell
Assistant Examiner—John C. Hanley
Attorney, Agent, or Firm—John E. Reilly

[57] ABSTRACT

The removal and separation of bone marrow cells for the purpose of analysis is carried out in a minimum number of steps by interposing a filtration chamber between a bone marrow needle and aspirator, withdrawing bone marrow particles together with sinusoidal blood through the filtration chamber so as to filter out or separate the bone marrow particles from the blood, and thereafter opening the filtration chamber to expose the particles for removal from the filter. The filtration chamber is constructed to define a fitting which can be releasably but sealingly connected at one end to the end of the needle and at the opposite end to the aspirator or syringe so that the necessary vacuum can be established and maintained for withdrawal of the specimen through the chamber without danger of contamination; and a seating surface within the chamber is so formed as to facilitate placement of a filter pad to collect the bone marrow particles and expose the particles for removal when the chamber is opened.

10 Claims, 8 Drawing Figures

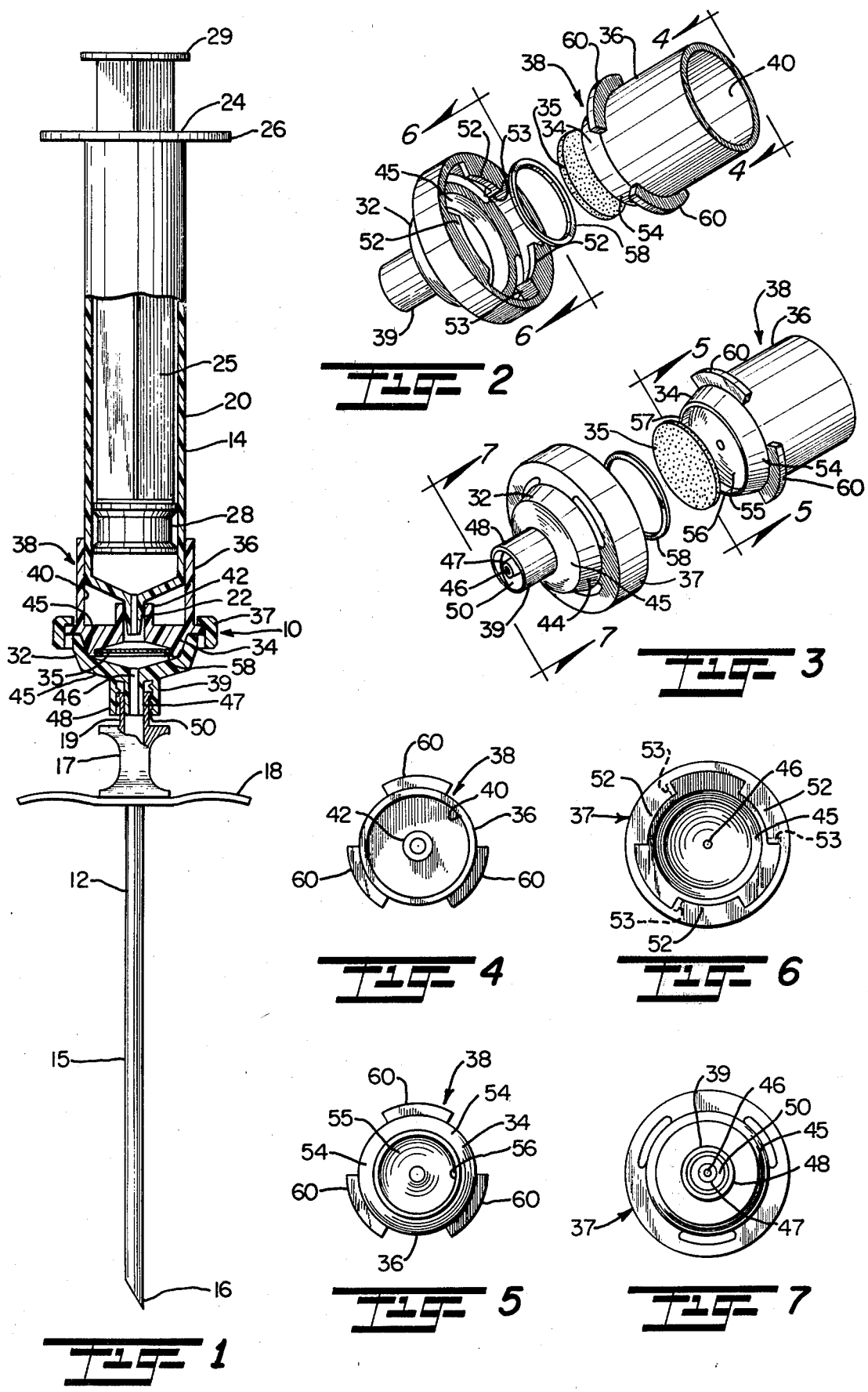

METHOD AND APPARATUS FOR BONE MARROW CELL SEPARATION AND ANALYSIS

This invention relates to a novel and improved method and apparatus for the separation and recovery of bone marrow cells or particles for the purpose of clinical analysis.

BACKGROUND OF THE INVENTION

Bone marrow examinations have been conducted either by blood clotting or filtration of the blood to recover the cells or specimens. In the former, the aspirated marrow particles which are removed with the blood are separated by clotted blood. In the filtration technique, the particles are recovered with the sinusoidal blood that are filtered from the blood for analysis. A number of publications discuss these procedures and their relative merits. For instance, "Bone Marrow Histology, Aspiration versus Biopsy", by Drs. A. M. Rywlin and B. Drewinko, A.J.C.P., pp. 617-618, Vol. 66, September, 1976; *Letters to the Editor,* "The Relative Merits of Bone Marrow Biopsy and Particle Section Technics", by Drs. R. S. Neiman, A. Coppola and T. Athanassiades, A.J.C.P., pp. 308-309, Vol. 67, No. 3; and "Bone Marrow Examinations", by Dr. B. O'Neill, pp. 21-22, The Medical Journal of Australia, Jan. 13, 1979.

In the conventional procedure, a bone marrow needle is inserted with a trocar into a bone marrow cavity at the intended site. An aspirator is then attached to the exposed end of the needle whereby application of a vacuum will induce the removal of sinusoidal blood along with any dislodged particles of the bone marrow through the needle into the aspirator. The aspirator is then removed and the blood passed through a suitable filtering device or onto a glass plate to aid in removal of any of the bone marrow particles from the blood. These particles are then placed or smeared on a slide for analysis.

In filtering the bone marrow particles from a quantity of blood recovered from the bone marrow, it may be difficult to obtain an adequate specimen for analysis. Also it requires the collection of the blood in a container such as a syringe followed by removal and separate filtration and is therefore time-consuming. Thus, if the specimen is inadequate, the entire procedure must be repeated and can cause a great deal of unnecessary discomfort to the patient as well as increased expense.

Various devices have been utilized in other medical or surgical procedures in which cells or tissue are withdrawn by vacuum onto a filter, then the filter removed and the sample scraped onto a slide for analysis. For example, representative U.S. patents are those to Molomut et al U.S. Pat. No. 3,224,434; Denis U.S. Pat. No. 3,889,682; and Baumgarten, U.S. Pat. No. 3,889,657.

Other devices employ a vacuum for removal of a liquid such as saliva in dental surgery and employ a filter or trap to separately collect the foreign particles. See, for example, U.S. patent to Berger, U.S. Pat. No. 3,706,305; Carritt et al U.S. Pat. No. 3,000,805; and Wiley U.S. Pat. No. 4,083,706. However, in these cases the filter or trap is employed more for the purpose of collecting foreign matter on a filter, but are not concerned with removal of the foreign matter from the filter or analysis of the foreign matter.

Other instruments have been devised for removal of the blood from a vein by injecting a needle into the vein and applying a vacuum to draw the blood into a syringe or container. For example, see U.S. patent to Worrall, Jr., U.S. Pat. No. 3,382,865; Sachs U.S. Pat. No. 3,965,889; and Bridgman U.S. Pat. No. 3,833,000. However in the past the vacuum or aspiration devices which include a trap for recovery of foreign matter are not so devised that fine particles can be selectively collected on the surface of a filter within a vacuum chamber in the path of the flow of blood from the bone marrow site, following which the chamber can be opened to immediately expose the filter and particles collected on the filter for removal.

SUMMARY OF THE INVENTION

It is therefore an object of the present invention to provide for a novel and improved cell separation device which is capable of filtering the cells out of the blood as the blood is withdrawn from the body in an efficient and highly reliable manner.

It is another object of the present invention to provide for a novel and improved method and apparatus for filtering bone marrow particles from the blood as the blood and particles are withdrawn from the body.

Another object of the present invention is to provide a cell separation device which is capable of recovering the highest percentage of particles from the sinusoidal blood withdrawn from the bone marrow site in a minimum number of steps while minimizing the need for a biopsy needle.

A still further object of the present invention is to provide for a cell separation device which is economical to manufacture, is of relatively simple construction and easy to use as well as being comprised of a minimum number of parts which are trouble-free in operation.

In accordance with the present invention, it has been found that the removal and analysis of bone marrow cells or specimens is considerably more effective and reliable by filtering the particles from the sinusoidal blood as the blood is withdrawn from the bone marrow site. In the preferred form, the bone marrow needle and trocar are inserted into the bone marrow site from which the specimen is to be removed and the needle is advanced so that its pointed end is driven into the bone marrow cavity so as to dislodge cells or particles of the bone marrow for subsequent collection and recovery. A novel form of aspiration device in accordance with the present invention is then releasably locked to the exposed end of the needle which includes a filtration chamber in sealed relation to the needle and a generally barrel-shaped fitting which is adapted to releasably receive the end of a syringe. The syringe is placed in sealed relation to the end of the fitting so that rearward movement of the plunger through the syringe and away from the fitting will introduce a vacuum throughout the fitting and needle sufficient to withdraw the blood and dislodged particles from the bone marrow for outward flow through the chamber and into the syringe. The filtration chamber is formed by a cap releasably locked to the end of the needle, a generally barrel-shaped fitting which has an open end adapted to receive the leading end of the syringe in sealed relation thereto, and a raised filter support having a recessed seating surface which is sealed between the cap and the fitting. The seating surface is provided with a slight concavity in the direction of the syringe to facilitate placement of a filter pad thereacross so that when the barrel-shaped fitting is connected to the cap the filter is effectively sandwiched between the cap and seating surface in facing relation to the needle. A quantity of blood is removed through the chamber formed between the seating surface and cap into the syringe, and the bone marrow particles which are suspended in the sinusoidal blood are collected on the surface of the filter.

In the conventional bone marrow separation technique, an incision is made at the point above the bone from which a specimen is to be taken and a bone marrow needle inserted at the point of incision. Once the needle is properly located with respect to the bone, it is advanced into the bone to a depth to assure recovery of a bone marrow specimen. If there is any difficulty in obtaining a specimen with the conventional needle aspirator, a biopsy needle is inserted through the bone marrow needle and into the bone to an even greater depth. In any case, once the specimen is taken from the bone, the bone marrow needle is left in place and a syringe is directly attached to the end of the needle for removal of the bone marrow specimen together with any sinusoidal blood. In accordance with the present invention, however, once the bone is penetrated, the bone marrow trocar is removed and the chamber with filter attached in place is releasably attached to the exposed end of the needle and the syringe inserted in place behind the vacuum chamber. In this way, the filter is interposed in the path of blood flow through the needle so as to intercept any bone marrow particles while permitting the sinusoidal blood to pass through into the syringe. It has been discovered that the filtration procedure of the present invention virtually eliminates the need for a biopsy needle. Once a predetermined quantity of blood has been removed, the filter assembly is detached from the needle and the fitting unlocked so as to remove the filter portion from the cap whereupon the bone marrow particles are removed from the filter pad. These particles are then placed on a slide or glass slide and smeared for examination; also, some particles may be placed in a tissue fixative solution. The syringe and barrel fitting are then disposed of and it is not necessary to remove the filter pad from the fitting.

The above and other objects, advantages and features of the present invention will become more readily appreciated and understood from the foregoing detailed description of a preferred embodiment when taken together with the accompanying drawings, in which:

BRIEF DESCRIPTION OF THE DRAWINGS

FIG. 1 is a front view partially in section of a preferred form of needle aspirator device in accordance with the present invention;

FIG. 2 is an exploded view taken somewhat from the rear of the chamber and filter portion of the preferred form of invention;

FIG. 3 is an exploded view similar to FIG. 2 and taken somewhat from the front of the chamber;

FIG. 4 is a rear view taken about lines 4—4 of FIG. 2;

FIG. 5 is a front view taken about lines 5—5 of FIG. 3;

FIG. 6 is a rear view taken from lines 6—6 of FIG. 2;

FIG. 7 is a front view taken from lines 7—7 of FIG. 3; and

DETAILED DESCRIPTION OF THE PREFERRED EMBODIMENT

Figure 8:
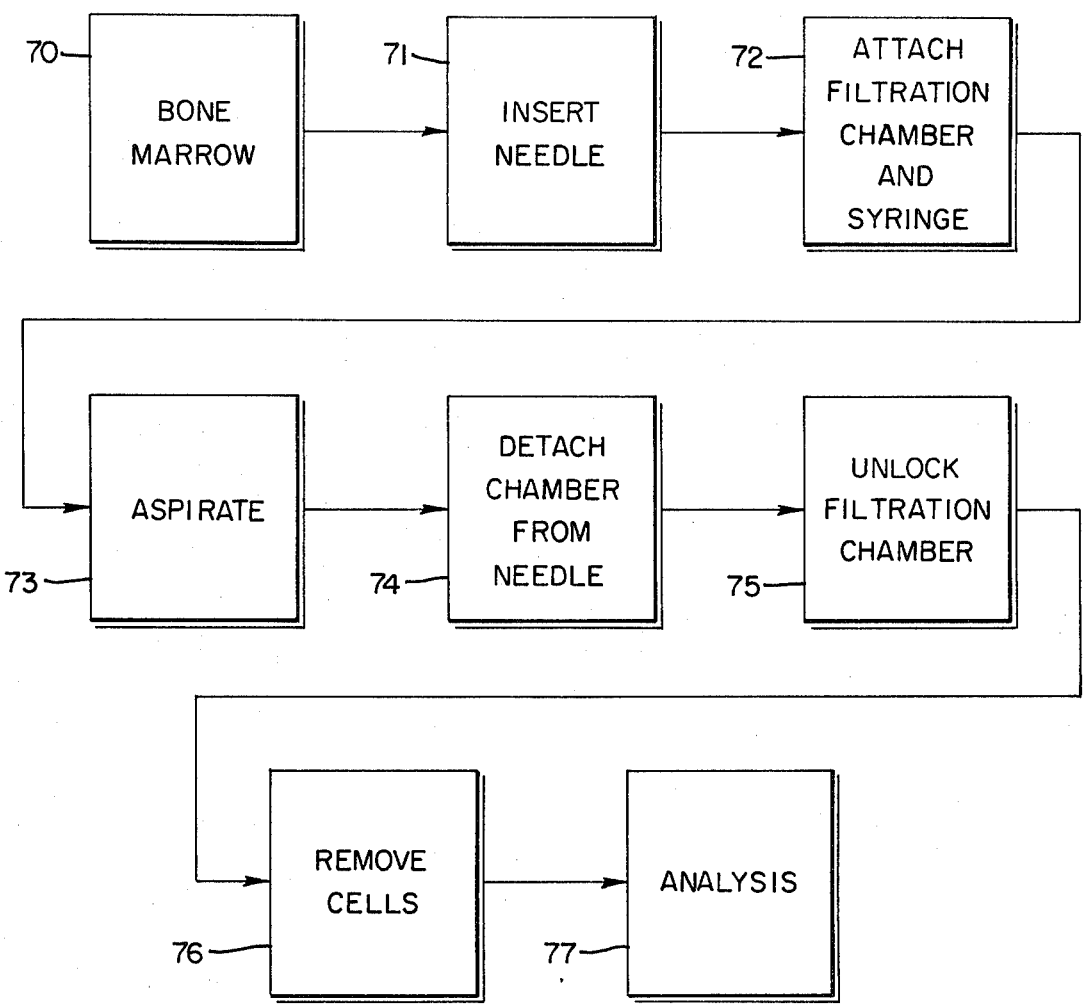
FIG. 8 is a flow diagram illustrating the succession of steps followed in the practice of the preferred method of the present invention.

There is illustrated in FIG. 1 a preferred embodiment of the present invention and specifically wherein a filtration chamber 10 is secured in assembled relation to a surgical needle 12 and aspirator 14 for the purpose of carrying out bone marrow cell separation procedures. The needle 12 is of conventional construction and representative of various types of needles which are employed in the removal of cells or particles from bone marrow. Typically, the needle is comprised of an elongated tubular shank portion 15 which terminates at one end in a tapered or pointed end portion 16 which is capable of penetrating the bone and of dislodging particles of bone marrow for withdrawal through the hollow interior of the needle. The opposite end of the needle includes a handle 17 affixed in surrounding relation to the end of the needle, the handle having a suitable shield or guard 18 and an externally threaded connecting end portion 19 which is of reduced diameter with respect to the handle 17.

The aspirator or syringe 14 is of conventional construction and, for example, may be of the disposable type having an outer elongated tubular shell 20 terminating at its leading end in a generally nozzle-shaped nose 22 and its opposite end 24 being open and adapted to receive a plunger or piston member 25. Typically, a flange 26 is disposed at the rearward end 24 of the outer shell 20 and the plunger includes a forward piston end portion 28 which is dimensioned to establish sealed engagement with the inner wall of the shell 20 while being slidable therethrough when force is applied to the rearward end 29 of the plunger. This type of syringe typically is utilized to expel fluids contained in the hollow interior of the shell through the leading end 22; but in the present invention is employed as an aspirator so that rearward movement or retraction of the plunger through the shell will create a negative pressure or vacuum in the space ahead of the piston end 28 so as to induce fluid or solid matter to pass outwardly through the needle 12 and the filtration chamber 10 into the syringe. Indeed, in conventional bone marrow cell removal procedures, ordinarily the bone marrow particles and blood are withdrawn or collected in the interior of the syringe or aspirator, then by a separate filtering procedure or other separation techniques, the bone marrow particles are separated from the blood.

In accordance with the present invention, the preferred form of filtration chamber 10 is comprised of a forwardly convergent needle-connecting section or cap 32, an intermediate filter support portion 34 for a filter 35 and a rearwardly extending annular body section or fitting 36, the needle-connecting section 32 and annular body 36 being releasably interconnected by coupling portions 37 and 38 in sealed relation to one another. The needle-connecting section or cap 32 has a forward connector 39 to establish a sealed but releasable connection to the needle 12; and the hollow interior 40 of the annular body 36 is dimensioned to sealingly but releasably receive the forward end of the shell 20 with the leading end 22 of the aspirator 14 being insertable into a central bore 42 formed in the filter support portion 34 in rearward spaced relation to the filter 35.

Specifically referring to FIGS. 2 and 3, the needle-connecting section 32 is of generally cup-shaped or conical configuration so as to define an outer peripheral wall 44 on its interior surface, which is relatively steeply inclined, and forward end wall 45 which slopes at a more gradual angle into a central bore 46. Connector 39 has inner and outer concentric tubular extensions 47 and 48, respectively, which project forwardly and define a space 50 therebetween for insertion of the reduced end 19 of the needle into sealed engagement between the tubular extensions. A positive lock is established between the tubular extensions 47 and 48 and the reduced extension 19 by forming threads along the inner wall of the outer extension 48 which will mate with the external threads on the extension 19. The rearward or trailing end of the cap 32 terminates in the coupling 37 which is in the form of an annular or ring-like member having radially inwardly projecting ribs 52 at circumferentially spaced intervals, the ribs intruding from the rearward edge of the outer wall of the coupling 37 and each provided with a forwardly directed lip 53 at one end of each rib.

The filter support 34 preferably is formed as a unitary or integral part of the annular body section 36 and is defined by a forwardly tapered external wall 54 in surrounding relation to a generally concave seating surface 55, the seating surface being recessed or inset slightly within the wall 54 so that the leading end of the support 34 forms a ledge 56 in surrounding relation to the seat 55. The filter support also includes a rearward cylindrical extension in surrounding relation to the central bore 42 which is sized to permit close-fitting insertion of the nozzle-shaped extremity 22 of the syringe. The filter 35 is sized for insertion across the seating surface 54 and within the ledge 56 and for example may suitably consist of a Telfa pad having a pore size on the order of 18 to 30 microns so as to be sufficiently small as to prevent passage of any bone marrow particles with blood into the aspirator 14. Thus the filter pad is preferably in the form of a disk which is of a thickness to fit snugly within the inner ledge 56 formed between the wall 55 and concave seating surface 54. In addition, a Teflon ring or washer 58 is adapted to be positioned over and along the outer periphery of the filter pad 35 in snug-fitting engagement with the inner ledge 56 whereby to retain the filter pad securely in place.

The male coupling portion 38 is defined by a plurality of circumferentially extending, radially outwardly projecting ribs 60 on the external wall surface of the annular body section 36 at the base of the external wall 54 of the filter support portion 34. The ribs are of a length corresponding to the spacing between the intruding ribs 52 of the female coupling portion 37 and are dimensioned to have an external diameter such that they are free to pass through the spaces between the intruding ribs. Further, the ribs 60 are given a thickness corresponding to the depth of the space between the intruding ribs 52 and the rearward edge of the cup-shaped portion 44 of the needle-connecting section 32 whereby the ribs 50 may be inserted axially for a distance sufficient to clear the ribs 37, then by twisting the body section 36 will slide into locking disposition behind the intruding ribs 37. In order to insure complete registry between the ribs 60 and 37, the body section 36 is twisted until the ribs abut the lips or dogs 53. In the locked or assembled relation as illustrated in FIG. 1, the tapered wall portion 54 of the filter support 34 will move into full engagement with the outer wall 44 of the conical portion 32 so as to establish a sealed relationship therebetween; and thus a sealed chamber is formed between the concave interior of the needle-connecting portion 32 and the seating surface 55 of the filter support 34 with the filter pad 35 spaced from the concave interior of the portion 32 by the sealing ring 58.

As a preliminary to carrying out the method of the present invention, an incision is made in the skin directly above the site or point at which the bone marrow is to be removed and which is generally designated at 70 in FIG. 5. A bone marrow needle is inserted through the incision to serve as a guide for insertion of the needle aspiration device, as represented at 71; and once the needle is properly located with respect to the bone, it is inserted into the bone to a depth to penetrate into the bone marrow cavity and to break off small particles of the bone marrow, the bone marrow needle being generally of the type illustrated in FIG. 1 and designated at 12. In either case, once the bone marrow needle has penetrated into the bone marrow cavity, a filtration chamber 10 is releasably locked to the reduced end 19 of the needle as described, and a syringe 14 is releasably inserted through the cylindrical end section or fitting 36 of the filtration chamber with its leading end 23 inserted in sealed relation to the bore 42 as represented at 72. The syringe is inserted in place with the plunger 29 in an advanced position within the chamber 20, as illustrated in FIG. 1, so that retraction of the plunger will create a vacuum or negative pressure sufficient to withdraw the bone marrow particles along with sinusoidal blood through the needle and filtration chamber, which step is represented at 73. The filter pad 35 will collect or trap any solid particles flowing with the sinusoidal blood on its surface while permitting the blood to continue through the chamber into the syringe. Once the desired quantity is collected, the needle-connecting end section 32 is disconnected from the needle, as at 74; and the coupling portions 37 and 38 are unlocked and specifically in such a way as to permit removal of the filter support 34 and attached filter 35 from the needle-connecting end section 32 so as to expose the bone marrow particles which have collected on the surface of the filter pad, as represented at 75.

The bone marrow particles may be collected or removed from the filter pad by picking them off with a suitable scalpel or knife as represented at 76. In order to perform clinical analysis, as represented at 77, some of the particles can be placed on a slide or coverslip and smeared for staining and immediate examination, while other particles can be placed in a tissue fixative solution, such as, formaldehyde or Zenker's solution for preparing permanent slides in the usual manner. The filtration chamber and syringe are preferably made of disposable materials and may be discarded once the bone marrow particles have been removed from the pad.

Preferably, the connecting end portion 32, filter support 34 and syringe support 36 are all composed of a plastic material having relatively high strength but with limited resiliency, such as, a high density polypropylene, manufactured and sold under the trademark Profax 6623, by Hercules Powder Company, of Los Angeles, Calif. The retention ring 58 when placed on the filter pad is preferably of a thickness to be flush with the outer edge of the wall 54. In this way, the ring 58 will securely retain the filter pad in place and facilitate removal of the bone marrow particles therefrom.

It is to be understood from the foregoing that while a preferred form of method and apparatus of the present invention have been set forth, it should be appreciated by those skilled in the art that various modifications, changes and adaptations may be made without departing from the scope of the present invention as defined by the following claims.

I claim:

1. A bone marrow separation apparatus adaptable for separation of bone marrow particles from sinusoidal blood wherein a needle provided with opposed forward and rearward ends has its forward end inserted into a bone of a mammal at the desired site of removal of the bone marrow particles, comprising:
   a filtration chamber including a hollow needle-connecting section converging toward said needle, said needle-connecting section including means to effect a positive but sealed connection with said rearward end of said needle while being in fluid communication with the hollow interior of said needle;
   a filter support member disposed in said filtration chamber having a seating surface disposed in facing relation to said needle-connecting section and provided with a central bore extending through said seating surface in communication with the interior of said filtration chamber, and a filter member positioned in said filtration chamber between said seating surface and said needle-connecting section;
   an annular support wall connected in surrounding relation to said filter support member for extension in a direction away from said needle-connecting section, said annular support wall disposed in outer spaced concentric relation to said central bore;
   coupling means releasably interconnecting said needle-connecting section and said filter support member with said filter member interpositioned therebetween; and
   a syringe inserted into snug-fitting relation to and within said annular support wall, said syringe having a leading end including a nozzle thereon aligned with and inserted into said central bore in open fluid communication with the interior of said filtration chamber including means in said syringe to induce the withdrawal of sinusoidal blood and bone marrow particles from said needle through said filtration chamber whereby said bone marrow particles are separated from the blood by said filter member as the blood is withdrawn into said syringe.

2. A bone marrow separation apparatus according to claim 1, said needle-connecting section including a concave interior wall provided with a central bore therein, and said filter support member including a convergent wall adapted to move into registry with said concave interior wall of said needle-connecting section.

3. A bone marrow separation apparatus according to claim 2, said filter support member provided with an annular ledge in surrounding relation to said filter support and a sealing ring disposed on said seating surface of said filter support member in facing relation to said needle-connecting section.

4. A bone marrow separation apparatus according to claim 1, said filter support member including a tapered wall forming a continuation of said annular wall and said seating surface being concave and recessed within said tapered wall portion.

5. A bone marrow separation apparatus according to claim 4, said filter support member including a cylindrical extension forming said central bore in said seating surface, said nozzle being inserted into said cylindrical extension.

6. A bone marrow separation apparatus according to claim 1, said coupling means including male coupling elements protruding in a radial outward direction from said annular wall and female coupling elements including a ring-like member on said needle-connecting section provided with radially inwardly extending elements adapted to interlockingly but releasably engage said male coupling elements.

7. In a bone marrow separation apparatus adaptable for separation of bone marrow particles from sinusoidal blood wherein a hollow needle is inserted into the bone at the desired site of removal of the bone marrow particles, a filtration chamber includes a needle-connecting portion having a hollow cylindrical body converging toward said needle to define a concave internal wall terminating in an end surface, said surface provided with means to effect a positive but sealed connection with the end of said needle opposite said bone inserting end while being in fluid communication with the hollow interior of said needle, and a syringe is positioned at one end of said chamber opposite to said end surface of said body in open fluid communication with the interior of said filtration chamber whereby to induce the withdrawal of sinusoidal blood and bone marrow particles through said chamber, the improvement comprising:
   a filter support member including a seating surface in facing relation to said needle-connecting portion, a wall portion tapering toward said needle-connecting portion and terminating in an annular ledge in surrounding relation to said seating surface, and an annular wall extending from one end of said tapered wall portion opposite to said annular ledge, said syringe being inserted into said annular wall into communication with the interior of said filtration chamber through a central bore formed in said seating surface, and coupling means including co-operating male and female coupling elements between said needle-connecting portion and said tapered wall portion to interlockingly but releasably interconnect said filter support member to said needle-connecting portion with said tapered wall portion engaging said concave internal wall of said needle-connecting portion along it substantial length whereby to establish sealed engagement between said tapered wall portion and said concave internal wall, said male coupling elements protruding in a radial outward direction from said tapered wall portion and said female coupling element including a member on said needle-connecting portion with radially inwardly extending elements adapted to interlockingly but releasably engage said male coupling elements, and a filter pad member positioned to extend across said seating surface within said filtration chamber.

8. In a bone marrow separation apparatus according to claim 7, said annular wall defined by a generally barrel-shaped fitting disposed in outer surrounding relation to said filter support member, said fitting adapted to receive said syringe and to support said syringe in communication with said filtration chamber.

9. In a bone marrow separation apparatus according to claim 7, including a sealing ring member removably disposed of said filter pad and sandwiched between said filter pad and the concave interior of said needle-connecting section.

10. In a bone marrow separation apparatus according to claim 9, said filter pad having a mesh size to permit the flow therethrough of sinusoidal blood while preventing the passage of any solid particles therethrough which are entrained in the blood.

* * * * *

UNITED STATES PATENT AND TRADEMARK OFFICE
CERTIFICATE OF CORRECTION

PATENT NO. : 4,366,822

DATED : January 4, 1983

INVENTOR(S) : John H. Altshuler

It is certified that error appears in the above—identified patent and that said Letters Patent is hereby corrected as shown below:

```
Column 5, line 34, after "with" add -- the --.
Column 5, line 56, cancel "50" and substitute
                   -- 60 --.
Column 5, line 61, cancel "the"  (third occurrence)

Claim 7, Column 8, line 41, cancel "it" and sub-
                   stitute -- its --.
Claim 9, Column 8, line 60, cancel "of" and sub-
                   stitute -- on --.
```

Signed and Sealed this

Fifteenth Day of March 1983

[SEAL]

Attest:

GERALD J. MOSSINGHOFF

Attesting Officer

Commissioner of Patents and Trademarks